United States Patent
Yokoi

(10) Patent No.: US 10,363,002 B2
(45) Date of Patent: Jul. 30, 2019

(54) X-RAY CT IMAGE RECONSTRUCTION DEVICE, X-RAY CT IMAGE RECONSTRUCTION METHOD, AND X-RAY CT APPARATUS

(71) Applicant: HITACHI, LTD., Tokyo (JP)

(72) Inventor: Kazuma Yokoi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 16/099,492

(22) PCT Filed: Jun. 2, 2017

(86) PCT No.: PCT/JP2017/020708
§ 371 (c)(1),
(2) Date: Nov. 7, 2018

(87) PCT Pub. No.: WO2017/221673
PCT Pub. Date: Dec. 28, 2017

(65) Prior Publication Data
US 2019/0105002 A1    Apr. 11, 2019

(30) Foreign Application Priority Data

Jun. 21, 2016 (JP) .................. 2016-122391

(51) Int. Cl.
*G06K 9/00* (2006.01)
*A61B 6/03* (2006.01)
(Continued)

(52) U.S. Cl.
CPC .............. *A61B 6/032* (2013.01); *A61B 6/482* (2013.01); *G06T 11/006* (2013.01); *A61B 6/5258* (2013.01); *G06T 2207/10081* (2013.01)

(58) Field of Classification Search
None
See application file for complete search history.

(56) References Cited

U.S. PATENT DOCUMENTS

2006/0109949 A1    5/2006  Tkaczyk et al.
2009/0310736 A1   12/2009  Ziegler et al.
(Continued)

FOREIGN PATENT DOCUMENTS

JP    2009-543603 A    12/2009
JP    2010-082031 A    4/2010

OTHER PUBLICATIONS

Vinicius C. Assis, et al., "Double Noise Filtering in CT:Pre- and Post-Reconstruction", Conference on Graphics, Patterns and Images (SIBGRAPI 2015), IEEE Computer Society, Jun. 2015.
(Continued)

*Primary Examiner* — Atiba O Fitzpatrick
(74) *Attorney, Agent, or Firm* — Mattingly & Malur, PC

(57) ABSTRACT

Base substance thickness projection estimation values (124) and base substance thickness projection estimation error values (125) of M (M≤N) base substances are estimated based on measured count projection values (121) using N energy windows for a subject. The base substance thickness projection estimated values (124) are updated such that a likelihood in accordance with a joint probability density of all of X-ray projection paths based on the base substance thickness projection estimated error values (125) increases. The obtained second base substance thickness projection assumed value (127) is subjected to back projection, thereby obtaining a base substance concentration image estimation value (128).

7 Claims, 8 Drawing Sheets

(51) Int. Cl.
*G06T 11/00* (2006.01)
*A61B 6/00* (2006.01)

(56) References Cited

U.S. PATENT DOCUMENTS

2015/0323685 A1* 11/2015 Nelson .................. G01T 1/1611
                                                250/370.08
2018/0144473 A1* 5/2018 Humbert ................ A61B 6/505

OTHER PUBLICATIONS

International Search Report of PCT/JP2017/020708 dated Jul. 25, 2017.

* cited by examiner

[Fig. 1]
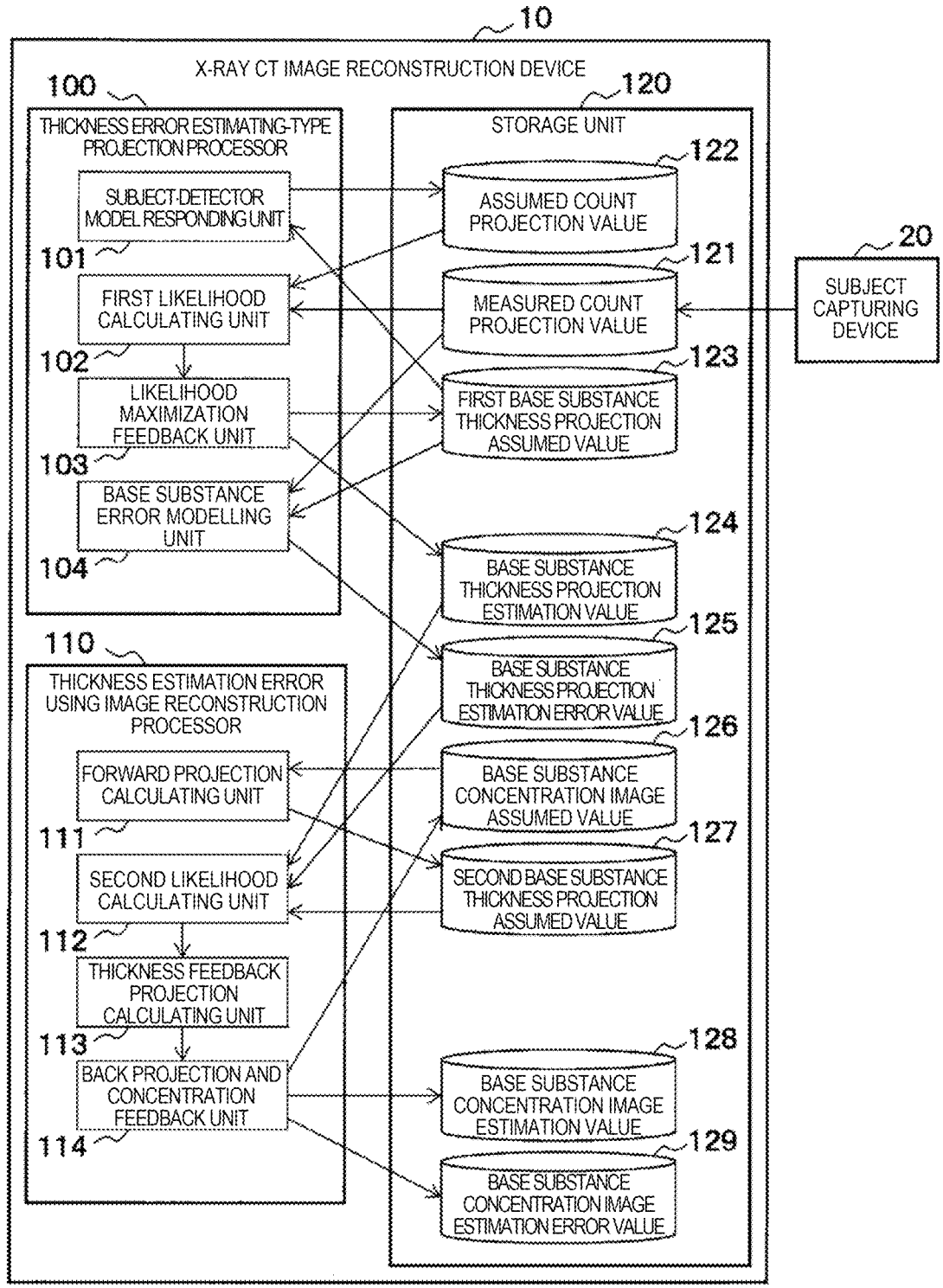

[Fig. 2]
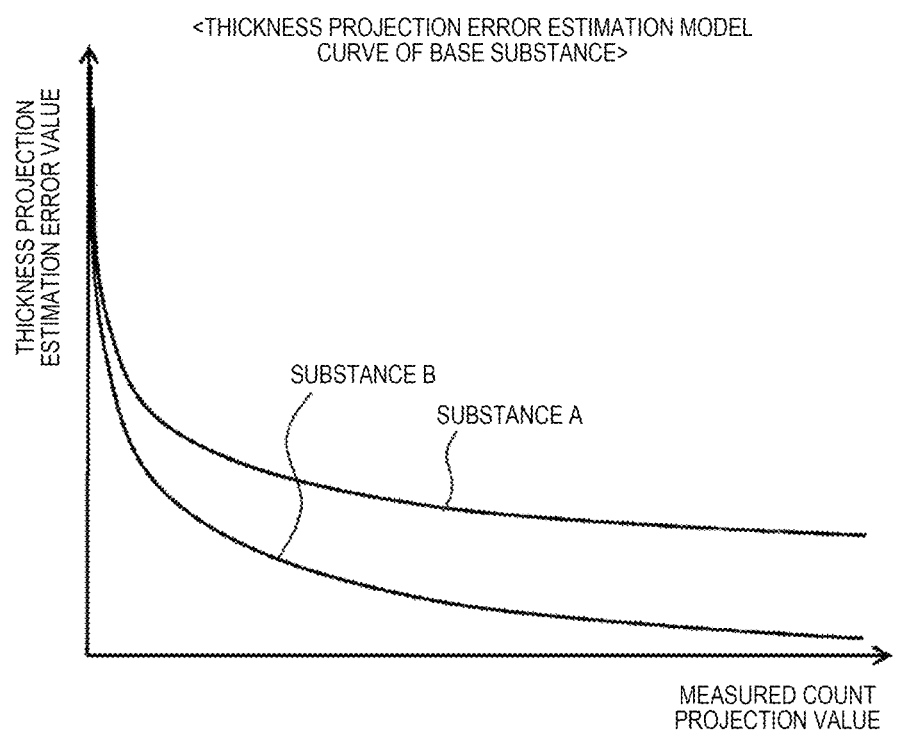

[Fig. 3]
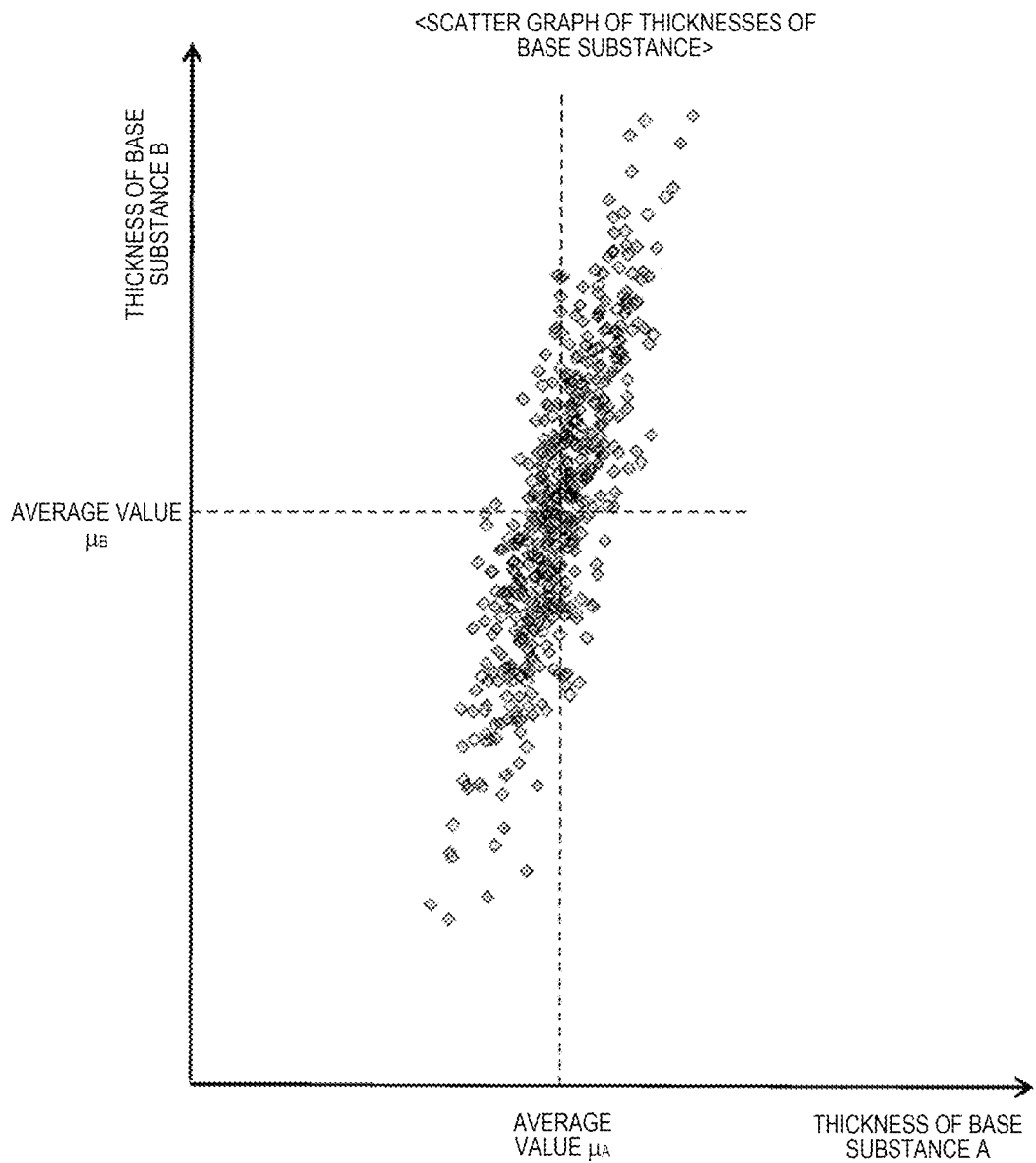

[Fig. 4]
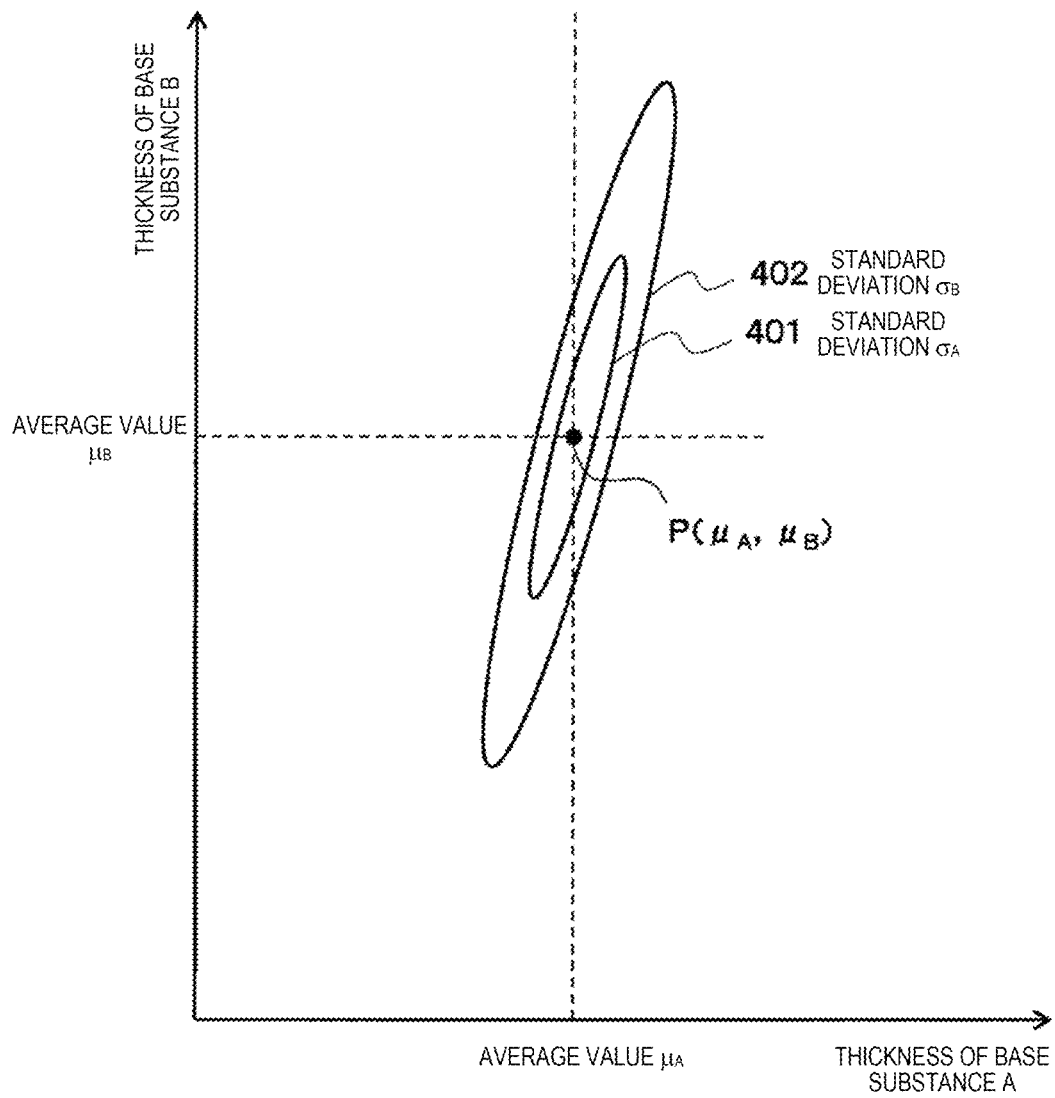

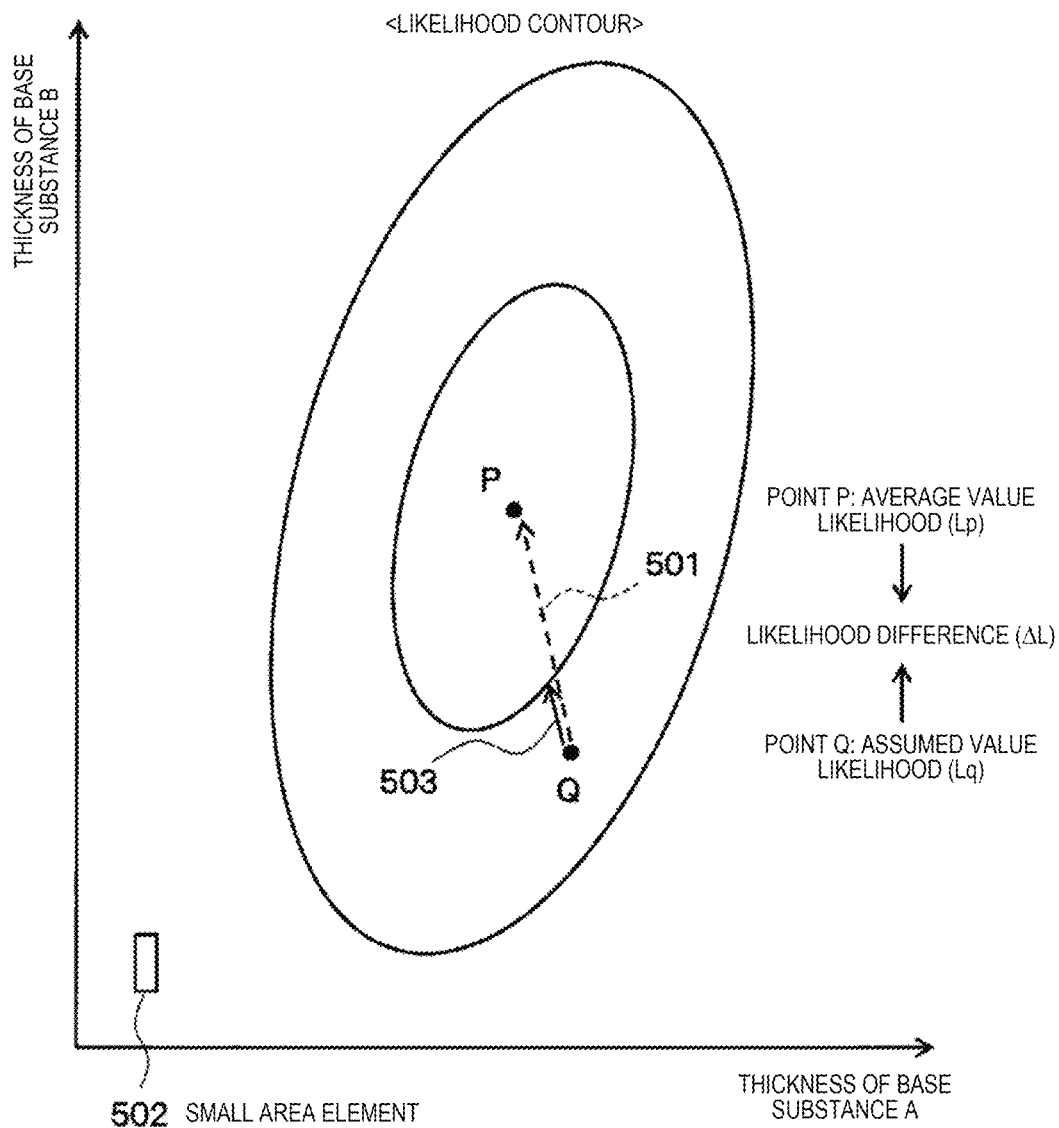

[Fig. 6]
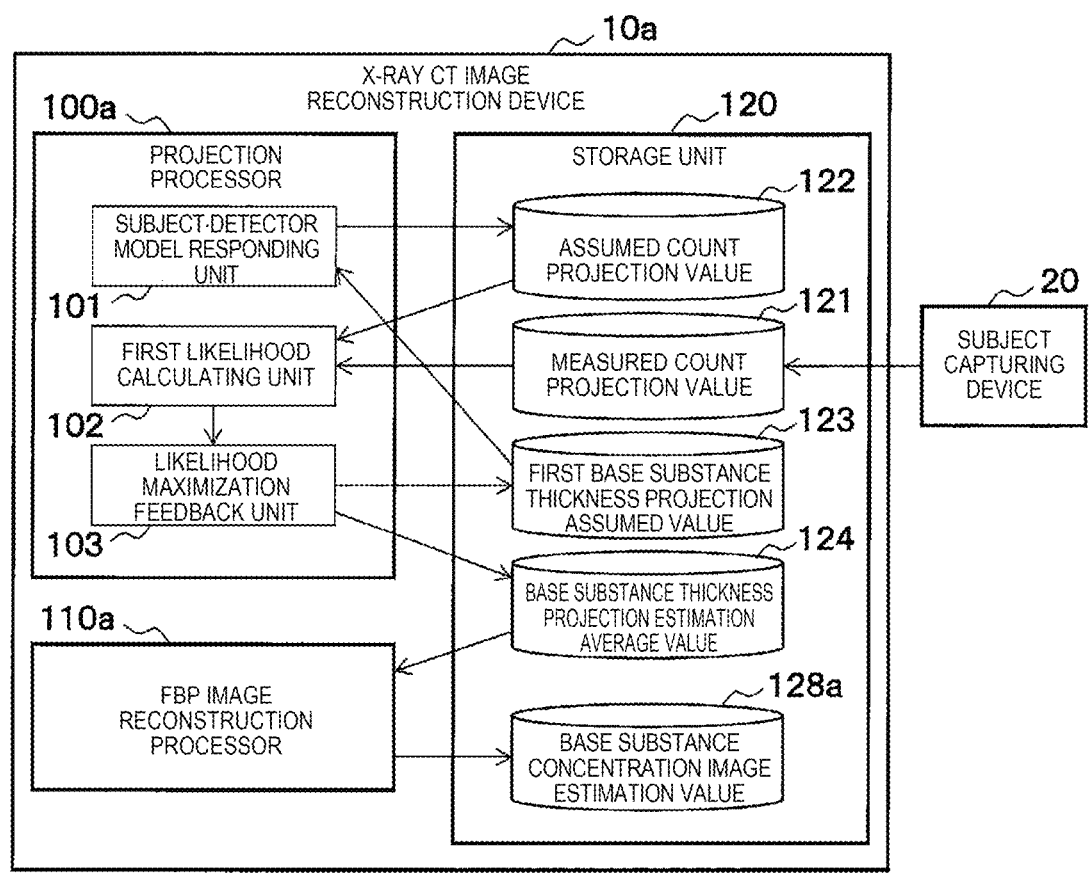

[Fig. 7]
(a) PRESENT INVENTION (COMPUTING IN CONFIGURATION IN Fig. 1)
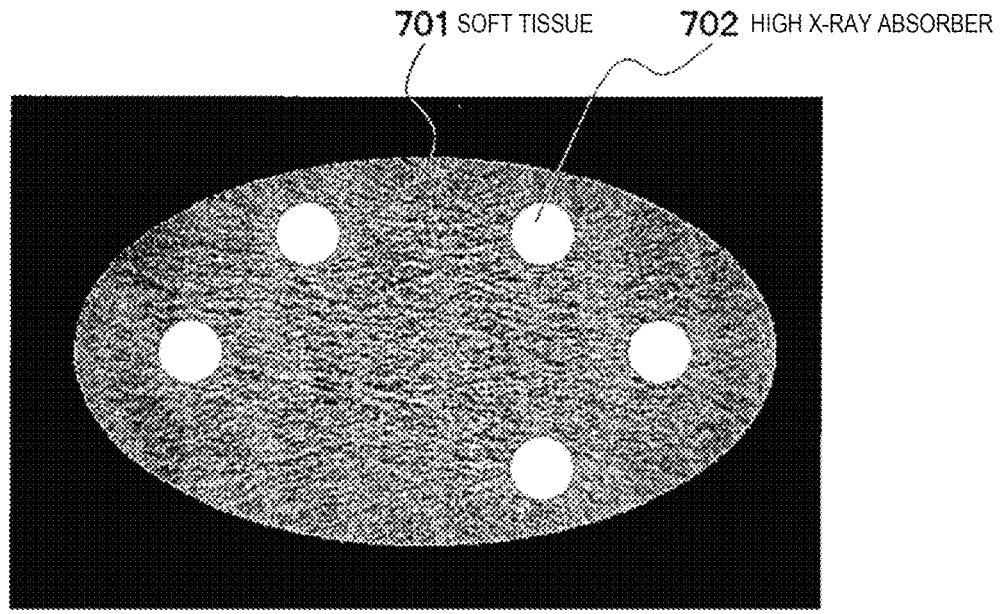
(b) COMPARATIVE EXAMPLE (COMPUTING IN CONFIGURATION IN Fig. 6)
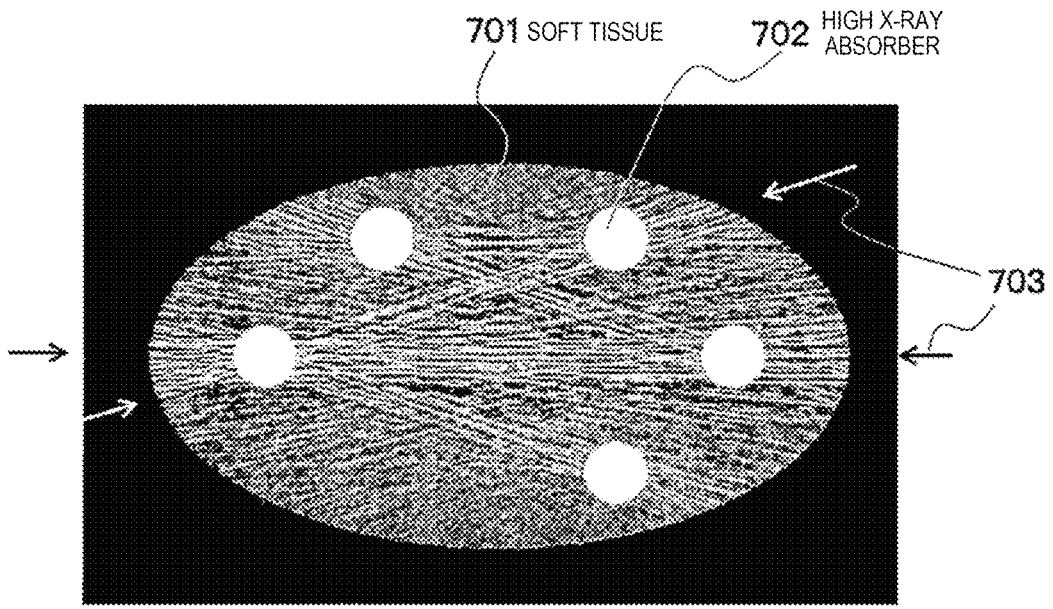

[Fig. 8]
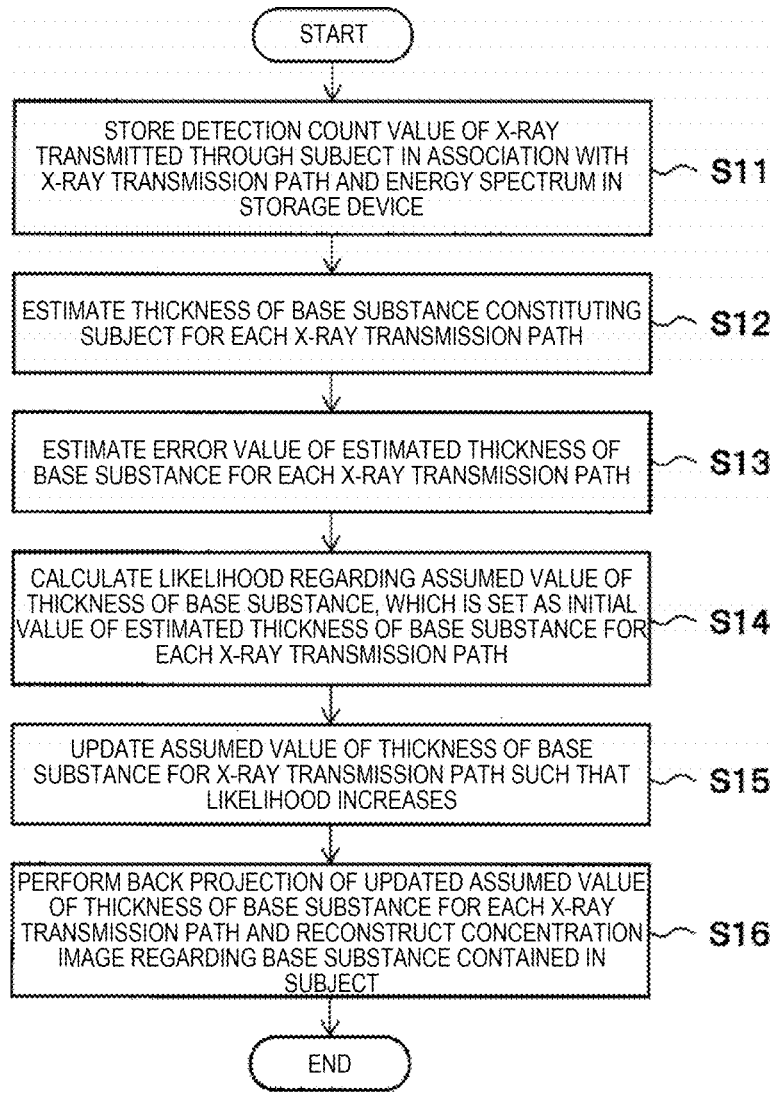

X-RAY CT IMAGE RECONSTRUCTION DEVICE, X-RAY CT IMAGE RECONSTRUCTION METHOD, AND X-RAY CT APPARATUS

TECHNICAL FIELD

The present invention relates to an X-ray computer tomography (CT) image reconstruction device, an X-ray CT image reconstruction method, and an X-ray CT apparatus.

BACKGROUND ART

In general, an X-ray CT apparatus in the related art has a configuration in which an X-ray detector in a current mode, in which energy information is not obtained, detects an X-ray photon group having a continuous (non-monochromatic) energy distribution that is generated by an X-ray tube. An X-ray attenuation coefficient has energy dependency that is specific to each of elements having different atomic numbers, and thus different energy distributions make it possible to obtain information related to the atomic numbers from a plurality of attenuation coefficients. However, in the general configuration of the X-ray CT apparatus in the related art, it is not possible to acquire information related to the atomic numbers.

In recent years, a technology for effectively using information by X-ray groups having a plurality of energy distributions has been developed, and examples of the technology include the following two technologies, largely. One technology is referred to as dual energy CT in which an X-ray detector has the current mode as is and uses two types of continuous energy distributions of X-rays, which are generated by two types of X-ray tube voltages. In addition, the other technology is referred to as photon counting CT (PCCT), spectral CT or the like and uses a pulse mode detector that is capable of acquiring energy information.

The X-ray CT apparatus finds a difference in ability of a substance for blocking an X-ray (an attenuation coefficient); however, dependency of an X-ray attenuation coefficient on energy varies depending on an element (atomic number). Hence, in a case of obtaining N types of energy information, it is possible to perform substance resolution into optional M (M≤N) substances having different effective atomic numbers, as base substances (for example, see PTL 1). Depending on whether the substance resolution is performed before returning to an image from projection information or after returning to the image, an image reconstruction method thereof includes two methods of a projection base method (pre-reconstruction method) and an image base method (post-reconstruction method) (for example, see NPTL 1). In the PCCT under a high-flux condition, a detection element is finer than that in the related art, and thus the projection base method is applied in order to process a complex spectral response, in general.

CITATION LIST

Patent Literature

PTL 1: Specification of US Patent Application Publication No. 2006/0109949

Non-Patent Literature

NPTL 1: ASSIS, V. C., SALVADEO, D. H. P., MASCARENHAS, N. D. A., LEVADA, A. L, M. "Double Noise Filtering in CT: Pre- and Post-Reconstruction", CONFERENCE ON GRAPHICS, PATTERNS AND IMAGES (SIBGRAPI 2015), IEEE Computer Society, June 2015

SUMMARY OF INVENTION

Technical Problem

The projection base method is advantageous in processing a complex spectral response of a measurement system; however, likelihood is considered for each of individual projection paths. Hence, an estimation value of the probability is estimated for each projection path. Thus, when the image reconstruction is performed by simple filtered back projection (FBP), a captured image having a low image quality, which has a strong influence of high statistical noise which remains on the projection path in a low count condition (NPTL 1).

An object of the present invention is to provide an X-ray computer tomography (CT) image reconstruction device, an X-ray CT image reconstruction method, and an X-ray CT apparatus in which it is possible to obtain an X-ray CT captured image having a high image quality.

Solution to Problem

According to the present invention, there is provided an X-ray CT image reconstruction device that is connected to an X-ray detector that measures a detection count value of X-ray transmitted through a subject, in response to each of N different energy spectra (N is an integer satisfying a relationship of N≥2), the apparatus including: storing means for storing the detection count value of X-ray measured by the X-ray detector, in association with each of X-ray transmission paths and each of the energy spectra when the X-ray is transmitted through the subject; base substance thickness estimating means for estimating, for each of the X-ray transmission paths, a thickness of each of M base substances (M is a positive integer satisfying a relationship of M≤N) constituting the subject, based on the detection count value of X-ray stored in the storing means; error estimating means for estimating an error value regarding the thickness of each of the base substances, based on the detection count value of X-ray; likelihood calculating means for calculating a likelihood which is an index of a probability of an assumed value of a thickness of each of the base substances for each of the X-ray transmission paths with the thickness of each of the base substances for each of the X-ray transmission paths, which has been estimated by the base substance thickness estimating means, as an initial value, based on the error value regarding the thickness of each of the base substances for each of the X-ray transmission paths, which has been estimated by the error estimating means; base substance thickness updating means for updating the assumed value of the thickness of each of the base substances for each of the X-ray transmission paths such that a likelihood that is to be calculated by the likelihood calculating means increases; and base substance concentration image reconstructing means for reconstructing a base substance concentration image regarding the M base substances of the subject by performing back projection of the assumed value of the thickness of each of the base substances for each of the X-ray transmission paths, which has been updated by the base substance thickness updating means.

Advantageous Effects of Invention

The present invention provides the X-ray CT image reconstruction device, the X-ray CT image reconstruction method, and an X-ray CT apparatus in which it is possible to obtain an X-ray CT captured image having a high image quality.

BRIEF DESCRIPTION OF DRAWINGS

FIG. 1 is a diagram showing an example of a configuration of an X-ray CT image reconstruction device according to an embodiment of the present invention.

FIG. 2 is a graph showing an example of a thickness projection error estimating model curve of a base substance.

FIG. 3 is a graph showing an example of a scatter graph of thicknesses of a plurality of base substances for each X-ray projection path, which is obtained in a process by a thickness error estimating-type projection processor.

FIG. 4 is a graph showing an example in which a relationship between a thickness of a base substance A and a thickness of a base substance B, which are shown in the scatter graph in FIG. 3, is modeled in a two-dimensional normal distribution.

FIG. 5 is a graph showing an example of a likelihood contour in a space which is represented by the thicknesses of the base substance A and the thicknesses of the base substance B.

FIG. 6 is a diagram showing an example of a configuration of a general X-ray CT image reconstruction device in the related art according to a comparative example.

FIG. 7 shows views of examples of base substance concentration images of a subject, FIG. 7(a) shows an example of a base substance concentration image computed by the X-ray CT image reconstruction device according to the embodiment of the present invention, and FIG. 7(b) shows an example of a base substance concentration image computed by the X-ray CT image reconstruction device according to the comparative example.

FIG. 8 is a diagram showing an example of a basic processing procedure for realizing, by a computer, an X-ray CT image reconstruction method according to an embodiment of the present invention.

DESCRIPTION OF EMBODIMENTS

Hereinafter, embodiments of the present invention will be described with reference to the figures. In the figures, the same reference signs are assigned to common constituent elements, and the repeated description thereof is omitted.

1. Configuration of X-Ray CT Image Reconstruction Device 10

FIG. 1 is a diagram showing an example of a configuration of the X-ray CT image reconstruction device 10 according to an embodiment of the present invention. The X-ray CT image reconstruction device 10 constitutes a part of an X-ray CT apparatus and generates a computed tomographic image of a subject from a measurement value of an X-ray transmission amount from a plurality of angular positions of the subject. An X-ray CT apparatus according to the embodiment is not shown in the figures; however, similar to a general X-ray CT apparatus in the related art, the X-ray CT apparatus is configured with a subject bed, a rotating gantry, an X-ray tube, an X-ray detector, a data collecting system, an image reconstruction device, an image display device, or the like. The embodiment is characterized by the image reconstruction device. Here, the image reconstruction device is referred to as the X-ray CT image reconstruction device 10 and a function and a configuration thereof will be described below.

Here, a subject capturing device 20 shown in FIG. 1 is a collective name of constituent elements such as the X-ray tube, the X-ray detector, and the data collecting system which measure and acquire a transmitted X-ray amount through the subject, of the constituent elements of the X-ray CT apparatus. In addition, in the embodiment, the X-ray CT image reconstruction device 10 reconstructs an image containing concentration information of base substances constituting the subject, and thus the X-ray detector is a pulse mode X-ray detector that is capable of obtaining energy information of an X-ray. The pulse mode X-ray detector is capable of sorting detected X-rays by a plurality of energy windows and acquiring a count value for each of the energy windows.

As shown in FIG. 1, the X-ray CT image reconstruction device 10 according to the embodiment is configured with, as main function blocks thereof, a thickness error estimating-type projection processor 100, an image reconstruction processor 110 using thickness estimation error, a storage unit 120, or the like.

Here, the thickness error estimating-type projection processor 100 configured with sub-blocks such as a subject•detector model responding unit 101, a first likelihood calculating unit 102, a likelihood maximization feedback unit 103, and a base substance error modelling unit 104. In addition, the thickness estimation error using image reconstruction processor 110 is configured with sub-blocks such as a forward projection calculating unit 111, a second likelihood calculating unit 112, a thickness feedback projection calculating unit 113, and a back projection and concentration feedback unit 114.

In addition, the storage unit 120 stores data of a measured count projection value 121, an assumed count projection value 122, a first base substance thickness projection assumed value 123, a base substance thickness projection estimation value 124, a base substance thickness projection estimation error value 125, a base substance concentration image assumed value 126, a second base substance thickness projection assumed value 127, a base substance concentration image estimation value 128, a base substance concentration image estimation error value 129, or the like.

In terms of hardware, the X-ray CT image reconstruction device 10 having such a functional configuration as described above is configured of a general computer including a calculation processing device not shown, a storage device (a main memory, a hard disk device, or the like), an input/output device (a keyboard, a display device, or the like). Functions of the units constituting the thickness error estimating-type projection processor 100 and the thickness estimation error using image reconstruction processor 110 are realized by executing a predetermined program stored in the storage device by the calculation processing device. In addition, the storage unit 120 is included in the storage device.

On the other hand, in the subject capturing device 20, an X-ray tube is not shown in the figure, the X-ray tube irradiates the subject with the X-rays, while rotating on a circumference with a position, at which the subject is disposed, as a substantial center. An X-ray, which is transmitted through the subject and is attenuated, is detected by an X-ray detector (not shown) disposed on a side opposite to the X-ray tube with the subject interposed therebetween. Here, the X-ray detector is configured of a plurality of X-ray detecting elements arranged in an array shape and is capable of detecting the X-ray by each of the X-ray detecting elements in a pulse mode and sorting pulses thereof by N types of energy windows (N is an integer equal to or larger than 2). The energy window means an energy spectrum that responds only to a specific energy zone with respect to incidence of the X-ray.

Hence, a measurement value, which is acquired by the X-ray detector, represents a count value of a pulse, and the count value is associated with a rotation position of the X-ray tube, an arrangement position of the X-ray detecting element constituting the X-ray detector, and an identification number of the energy window. The subject capturing device 20 transmits the count value of the X-ray which is measured by the X-ray detector to the X-ray CT image reconstruction device 10.

The X-ray CT image reconstruction device 10 receives the count value of the X-ray which is measured by the X-ray detector, which is transmitted from the subject capturing device 20, and stores the received count value as the measured count projection value 121 in the storage unit 120. In this case, the measured count projection value 121 has a configuration in which the count value of the X-ray is associated with the rotation position of the X-ray tube, the arrangement position of the X-ray detecting element, and the identification number of the energy window.

In this specification, information, which is designated at the rotation position of the X-ray tube and the arrangement position of the X-ray detecting elements, means an X-ray projection path, hereinafter. Hence, the measured count projection value 121 can be defined to have a configuration in which the count value of the X-ray is associated with the X-ray projection path and the identification number of the energy window.

2. Process in Thickness Error Estimating-Type Projection Processor 100

The thickness error estimating-type projection processor 100 computes the base substance thickness projection estimation value 124 regarding the subject and the base substance thickness projection estimation error value 125 that is information of error thereof from the measured count projection value 121 stored in the storage unit 120 and stores the values in the storage unit 120. Hereinafter, a thickness error estimating-type projection process in the thickness error estimating-type projection processor 100 will be described in detail. The thickness error estimating-type projection process is based on a projection base method in the related art.

Here, in a start of the thickness error estimating-type projection process, an initial value of the first base substance thickness projection assumed value 123 regarding the subject is associated with the X-ray projection path and the identification number of a base substance, and the initial value is stored in the storage unit 120. The initial value of the first base substance thickness projection assumed value 123 may be an average value that is not dependent on the X-ray projection path for each identification number of the base substance or may be any value obtained by a simple estimation process performed in advance.

First, the subject•detector model responding unit 101 reads the first base substance thickness projection assumed value 123 from the storage unit 120. Next, the subject•detector model responding unit 101 calculates an extent to which an amount of X-rays (the number of photons), with which irradiation from the X-ray tube is performed, is attenuated, for each X-ray projection path, by using the first base substance thickness projection assumed value 123 of each of M base substances. The number M of base substances is a positive integer (M≤N) equal to or smaller than N (the number of energy windows).

Further, the subject•detector model responding unit 101 calculates the count value for each X-ray projection path and energy window based on the calculation result and a preset spectral response characteristic of the X-ray detector. The computed count value is associated with the X-ray projection path and the identification number of the energy window and is stored as the assumed count projection value 122 in the storage unit 120.

Next, the first likelihood calculating unit 102 reads the measured count projection value 121 and the assumed count projection value 122 which are associated with the X-ray projection path and the identification number of the energy window from the storage unit 120. The Poisson statistics are assumed to have the read assumed count projection value as an average value and the measured count projection value as a realization value and a likelihood for each X-ray projection path is calculated. Preferably, the likelihood is used in a form of a log-likelihood because of a numerical range of numerical processing.

Next, the likelihood maximization feedback unit 103 updates thicknesses of the base substances for each X-ray projection path such that the likelihood increases, that is, the first base substance thickness projection assumed value 123. It is possible to use a general optimization method such as a conjugate gradient method using a gradient of a likelihood approximate to the first base substance thickness projection assumed value 123 at the time of calculation of the thickness of the base substance in the calculation of the thickness thereof such that the likelihood increases. The first base substance thickness projection assumed value 123 updated in this manner is associated with the X-ray projection path and is stored in the storage unit 120.

The processes of the subject•detector model responding unit 101, the first likelihood calculating unit 102, and the likelihood maximization feedback unit 103 described above are executed by being repeated at least twice. The likelihood maximization feedback unit 103 compares a likelihood obtained in the process of the first likelihood calculating unit 102 to a likelihood obtained in the same process that has been previously performed. In a case where an absolute value of a change amount or a change rate of the likelihood is equal to or smaller than a predetermined value, or in a case where the process of the repetition is executed over predetermined times, the process of the repetition is ended.

When the process of the repetition is ended, the likelihood maximization feedback unit 103 stores the last updated first base substance thickness projection assumed value for each X-ray projection path, at the time of the end of the process, as the base substance thickness projection estimation value 124 in the storage unit 120.

Next, the base substance error modelling unit 104 estimates a degree of an error of the last updated first base substance thickness projection assumed value 123 (that is, the base substance thickness projection estimation value 124) for each X-ray projection path and stores the degree of the error as the base substance thickness projection estimation error value 125 in the storage unit 120.

FIG. 2 is a graph showing an example of a thickness projection error estimating model curve of the base substance. In the graph in FIG. 2, the vertical axis represents a thickness projection estimation error value of the base substance (that is, an error value at the time of estimating a thickness estimation value of the base substance), and the horizontal axis represents the measured count projection value. In addition, the two curves represent the thickness projection error estimating model curves regarding a substance A and a substance B constituting the subject, for example. Information of the thickness projection error estimating model curves of the base substances are stored in the storage unit 120.

As shown in FIG. 2, in a case of almost all substances without being limited to the substance A or the substance B, the thickness projection estimation error value decreases as the measured count projection value increases. This can be obtained as a result based on a general principle of obtaining data having high accuracy (a low error) as the number of measurement data increases.

It is needless to say that a specific value or a mode of decrease of the thickness projection estimation error value varies depending on the base substances. In the embodiment, the thickness projection error estimating model curve as shown in FIG. 2 is prepared in advance depending on the base substance and is stored in the storage unit 120. The thickness projection error estimating model curve can be formed, based on a physical model or a statistical model of the base substance and can be formed by using measured thickness error data obtained in the past as prior information.

As described above, the base substance error modelling unit 104 is capable of obtaining the base substance thickness projection estimation error value 125 for each X-ray projection path based on the measured count projection value 121 for each X-ray projection path with reference to the thickness projection error estimating model curve (refer to FIG. 2).

3. Process in Thickness Estimation Error Using Image Reconstruction Processor 110

Next, contents of the thickness-estimation-error using image reconstruction process by the thickness estimation error using image reconstruction processor 110 is again described with reference to FIG. 1. The thickness estimation error using image reconstruction processor 110 computes the base substance concentration image estimation value 128 and the base substance concentration image estimation error value 129 based on the base substance thickness projection estimation value 124 and the base substance thickness projection estimation error value 125. The process is based on the image base method in the related art. However, since the process is executed in consideration of all of the likelihoods on all of the projection paths at the same time, a reconstruction image having a small statistical error is obtained.

In starting the process of the thickness estimation error using image reconstruction processor 110, the initial value of the base substance concentration image assumed value 126 needs to be set in advance. The base substance concentration image can be a display of a region of the subject, which corresponds to pixels of the reconstruction image, with composition ratios of base substances. In the embodiment, a value obtained by adding a slight difference to a value obtained by executing a simple filtered back projection (FBP) process to the base substance thickness projection estimation value 124 obtained as a process result by the thickness error estimating-type projection processor 100 is used as the initial value of the base substance concentration image assumed value.

The base substance concentration image assumed value 126 stored in the storage unit 120 includes the initial value and is updated by the process of the back projection and concentration feedback unit 114, whenever a series of processes of the forward projection calculating unit 111, the second likelihood calculating unit 112, the thickness feedback projection calculating unit 113, and the back projection and concentration feedback unit 114, which will be described below, are repeated.

First, the forward projection calculating unit 111 calculates thicknesses of the base substances of the subject for each X-ray projection path based on the base substance concentration image assumed value 126 stored in the storage unit 120 at the time and stores a result obtained by the calculation as the second base substance thickness projection assumed value 127 in the storage unit 120. The second base substance thickness projection assumed value 127 differs from the first base substance thickness projection assumed value 123 that is computed from the measured count projection value 121 in that the second base substance thickness projection assumed value is computed based on concentration (the base substance concentration image assumed value 126) of pixels on the subject image.

Next, the second likelihood calculating unit 112 calculates a likelihood for each X-ray projection path based on the second base substance thickness projection assumed value 127, the base substance thickness projection estimation value 124, and the base substance thickness projection estimation error value 125 which are stored the storage unit 120 at the time. Further, the second likelihood calculating unit 112 computes the likelihood according to the joint probability density of all of the X-ray projection paths. The joint probability density of all of the X-ray projection paths will be described below.

Here, the calculation of the likelihood for each X-ray projection path means calculation of a likelihood based on the Poisson statistics similar to the calculation of the likelihood by the first likelihood calculating unit 102. In other words, also including the case of calculating the likelihood by the first likelihood calculating unit 102, a likelihood is computed with a value, which is derived from an assumed value, as an average value and a value, which is derived from actual measurement, as a realization value. Here, the likelihood is computed with the base substance thickness projection estimation value 124, which is derived from actual measurement, as the average value and the second base substance thickness projection assumed value 127 as the realization value.

When a mode of the calculation of the likelihood is employed, it is possible to reduce costs for calculating an estimation error value because an estimation error value of the base substance thickness projection estimation value 124, which is derived from the actual measurement, is obtained as the base substance thickness projection estimation error value 125. In other words, when a series of processes from the forward projection calculating unit 111 to the back projection and concentration feedback unit 114 are executed, it is not necessary to compute an estimation error value corresponding to the error of the base substance thickness projection estimation value 124.

Subsequently, the thickness feedback projection calculating unit 113 calculates a change amount (feedback amount) of thickness of each of the base substances for each X-ray projection path based on the likelihood corresponding to the joint probability density of all of the X-ray projection paths, which has been calculated by the second likelihood calculating unit 112, such that the likelihood increases. Process contents of the thickness feedback projection calculating unit 113 are separately described with reference to FIGS. 3 to 5.

Next, the back projection and concentration feedback unit 114 changes the thickness of each of the base substances for each X-ray projection path, which has the second base substance thickness projection assumed value, based on a feedback amount of the thickness of each of the base substances for each X-ray projection path which has been calculated by the thickness feedback projection calculating unit 113. The changed thickness of each of the base substances for each X-ray projection path as back projection is subjected to back projection such that a concentration image for each base substance of the subject is computed. As a result, the base substance concentration image assumed value 126 stored in the storage unit 120 is updated.

The series of processes from the forward projection calculating unit 111 to the back projection and concentration feedback unit 114 are executed by being repeated at least twice. During the repetitive processes, the back projection and concentration feedback unit 114 compares a likelihood corresponding to the joint probability density of all of the X-ray projection paths, which has been obtained in the process of the second likelihood calculating unit 112 to a likelihood obtained in the same process that has been previously performed. In a case where an absolute value of a change amount or a change rate of both of the likelihoods is equal to or smaller than a predetermined value, or in a case where the process of the repetition is executed over predetermined times, the process of the repetition is ended.

Further, when the back projection and concentration feedback unit 114 ends the process of repetition, that is, when the likelihood reaches an approximation of the maximum value, the latest base substance concentration image assumed value 126 at the time is stored as the base substance concentration image estimation value 128 in the storage unit 120. In addition, the back projection and concentration feedback unit 114 stores an error value of the base substance concentration image estimation value 128 as the base substance concentration image estimation error value 129 in the storage unit 120 based on the likelihood corresponding to the joint probability density of all of the X-ray projection paths which is last obtained by the second likelihood calculating unit 112.

4. Regarding Calculation of Likelihood of Joint Probability Density of all of X-Ray Projection Paths FIG. 3 is a graph showing an example of a scatter graph of thicknesses of a plurality of base substances for each X-ray projection path, which is obtained in a process by the thickness error estimating-type projection processor 100. In other words, FIG. 3 can be described to show the scatter graph of the thicknesses of the plurality of base substances for each X-ray projection path which is stored as the base substance thickness projection estimation value 124. Here, for simplification of the description, the number M of the base substances is set as 2 (M=2), and the scatter graph represents a relationship between the thickness of the base substance A (the horizontal axis) and the thickness of the base substance B (the vertical axis).

In the scatter graph in FIG. 3, $\mu_A$ represents an average value that is the average value of thicknesses of the base substance A, which are obtained from the scatter graph, and $\mu_B$ represents an average value that is the average value of thicknesses of the base substance B. From the scatter graph, a relationship that will be described as a substantially two-dimensional normal distribution is found between the thicknesses of the base substance A and the thicknesses of the base substance B, and it is possible to estimate a constant correlation between both of the thicknesses.

FIG. 4 is a graph showing an example in which the relationship between the thicknesses of the base substance A and the thicknesses of the base substance B, which are shown in the scatter graph in FIG. 3, is modeled in a two-dimensional normal distribution. From the scatter graph in FIG. 3, it is not only possible to obtain the average value $\mu_A$ of the thicknesses of the base substance A and the average value $\mu_B$ of the thicknesses of the base substance B, it is but also possible to obtain standard deviations $\sigma_A$ and $\sigma_B$, and it is also possible to obtain a correlation coefficient $\rho$ between the thicknesses of the base substance A and the thicknesses of the base substance B.

In FIG. 4, a point P represents a position at which the average value of the thicknesses of the base substance A is $\mu_A$ and the average value of the thicknesses of the base substance B is $\mu_B$. In addition, ellipses 401 and 402 represent positions at which the standard deviations of the thicknesses of the base substance A and the base substance B correspond to $\sigma_A$ and $\sigma_B$, respectively. In other words, in the model in FIG. 4, at every position in a space configured of the thicknesses of the base substance A (the horizontal axis) and the thicknesses of the base substance B (the vertical axis), it is possible to define the standard deviation, that is, an error.

In FIG. 4, the number M of base substances is set as 2 (M=2); however, in a case of M≥3, a concept of a variance-covariance matrix is employed, and thereby it is possible to obtain a standard deviation of base substances or a correlation coefficient between a plurality of base substances.

FIG. 5 is a graph showing an example of a likelihood contour in a space which is represented by the thicknesses of the base substance A and the thicknesses of the base substance B. Here, a case is considered in which the number of base substances is 2 (M=2), and an average value of the base substance thickness projection estimation values 124, which are obtained when the process of the thickness error estimating-type projection processor 100 is ended, are the average value of the thicknesses of the base substances in the process of the thickness estimation error using image reconstruction processor 110. In this case, a vector from a position (point Q in FIG. 5) represented by the second base substance thickness projection assumed value 127, which is obtained in the process of the forward projection calculating unit 111, to a position (point P in FIG. 5) represented by the base substance thickness projection estimation value 124 is a thickness-feedback-direction vector 501.

As described above, an initial value of the base substance concentration image assumed value 126 uses a value obtained by adding a slight difference to a value obtained by performing the FBP process on the base substance thickness projection estimation value 124. Hence, the second base substance thickness projection assumed value 127, which is first obtained by the process of the forward projection calculating unit 111, is different from the base substance thickness projection estimation value 124, and thus it is possible to avoid a state in which the thickness-feedback-direction vector 501 is zero.

In addition, in the embodiment, the base substance thickness projection estimation error value 125 is already known with respect to the base substance thickness projection estimation value 124 for each X-ray projection path, and thus it is possible to set a probability density function of the thicknesses of the base substances for each X-ray projection path. Subsequently, a joint probability density function of the thicknesses of the base substances for all of the X-ray projection paths is obtained, and it is possible to define likelihoods for points in the space configured of the thicknesses of the base substance A and the thicknesses of the base substance B in FIG. 5, by the joint probability density function. Here, the probability density function means a function indicating a normal distribution that is identified by the average value and the standard deviation, and the probability density means a value obtained by the probability density function, for example. In addition, the joint probability density function means a probability density function indicating a multi-dimensional normal distribution that is identified by a covariance matrix value, in addition to the average value and the standard deviation, and the joint probability density means a value obtained by the joint probability density function.

In this case, when a small area element 502, which is determined by necessary thickness accuracy, is provided, it is possible to provide a likelihood difference ΔL to the point P and the point Q in FIG. 5. Here, when the likelihoods of the point P and the point Q are an average value likelihood Lp and an assumed value likelihood Lq, it is possible to determine a thickness feedback vector 503 that is calculated by the thickness feedback projection calculating unit 113, by using the likelihood difference ΔL (=|Lp−Lq|).

In this case, when the point P and the point Q have the same positional relationship, the likelihood difference ΔL decreases on a projection path having an increase in distribution of the base substance thickness projection estimation error value 125, and the likelihood difference ΔL increases on a projection path having a decrease in distribution thereof. Hence, when the likelihood difference ΔL is weighed in the calculation by the thickness feedback projection calculating unit 113, it is possible to preferentially process information of the X-ray projection path having small distribution.

In FIG. 5, the thickness feedback vector 503 is used when the thicknesses of the base substance A and the base substance B are updated in the repetitive process of the thickness feedback projection calculating unit 113, and a direction thereof is the same as that of the thickness-feedback-direction vector 501. In addition, the size of the thickness feedback vector 503 has a positive correlation with respect to both of the size of the thickness-feedback-direction vector 501 and the likelihood difference ΔL; however, the correlation thereof may be a linear shape or a non-linear shape. Further, a size of the thickness feedback vector 503 may be appropriately adjusted, depending on the times of process repetition.

Further, giving a random slight difference to the thickness feedback vector 503 by using an annealing method may be repeated, and a thickness of the base substances, which is the maximum value of the joint probability (likelihood) of all of the projection paths which is obtained each time of the repetition, may be the thickness of the base substances at the time of concentration image back projection calculation. In addition, the embodiment is not limited to the simple optimization (maximization) of only the likelihood as described above, and an optimization method in which a filtering function is also included so as to impose a penalty on a rapid change in an image approximation value, for example.

Also in a case of FIG. 4, since the average values $\mu_A$ and $\mu_B$ of the thicknesses of the base substances, the standard deviations σA and σB thereof, and the correlation coefficient ρ are defined even in the space configured of the thicknesses of the base substance A and the thicknesses of the base substance B, it is possible to define the likelihood. These are not obtained based on the base substance thickness projection estimation error value 125 that is calculated by the base substance error modelling unit 104 but is obtained based on the scatter graph in FIG. 3. However, the likelihood that is obtained from the scatter graph in FIG. 3 is considered to be substantially equal to the likelihood obtained in consideration of the joint probability density of all of the X-ray projection paths.

5. Comparative Example

FIG. 6 is a diagram showing an example of a configuration of a general X-ray CT image reconstruction device 10a in the related art according to a comparative example. As shown in FIG. 6, the X-ray CT image reconstruction device 10a according to the comparative example is configured with a projection processor 100a, an FBP image reconstruction processor 110a, and the storage unit 120. Hereinafter, a difference from the X-ray CT image reconstruction device 10 (refer to FIG. 1) according to the embodiment of the present invention will be described.

First, the projection processor 100a according to the comparative example does not include the base substance error modelling unit 104 that is provided in the thickness error estimating-type projection processor 100 in the embodiment. Therefore, the projection processor 100a computes the base substance thickness projection estimation value 124 but does not compute the base substance thickness projection estimation error value 125 (refer to FIG. 1). In other words, the base substance thickness projection estimation value 124 does not contain error information thereof.

Hence, the FBP image reconstruction processor 110a performs a simple FBP image reconstruction process by using the base substance thickness projection estimation value 124 so as to compute only a base substance concentration image estimation value 128a and does not perform the repetitive process for improving an image quality by using error information. Therefore, in the comparative example, in a case where the base substance thickness projection estimation value 124 of a certain X-ray projection path has a large error, the image quality of the base substance concentration image estimation value 128a is degraded due to an influence of the large error. For example, a streak artifact or the like as shown in FIG. 7 occurs in some cases.

FIG. 7 shows views of examples of base substance concentration images of the subject, FIG. 7(*a*) shows an example of a base substance concentration image computed by the X-ray CT image reconstruction device 10 according to the embodiment of the present invention, and FIG. 7(*b*) shows an example of a base substance concentration image computed by the X-ray CT image reconstruction device 10a according to the comparative example. In FIG. 7, the subject is configured of soft tissue 701 containing a lot of water or the like and a high X-ray absorber 702 such as a bone that absorbs the X-ray well.

As shown in FIG. 7(*a*), in particular, the artifact or the like does not appear on the base substance concentration image computed by the X-ray CT image reconstruction device 10 according to the embodiment of the present invention. In contrast, as shown in FIG. 7(*b*), stripe-shaped streak artifacts are generated in directions represented by arrows 703 on the base substance concentration image computed by the X-ray CT image reconstruction device 10a according to the comparative example.

In FIG. 7(*b*), two high X-ray absorbers 702 are present on an X-ray projection path represented by the arrow 703 along which the streak artifacts are generated. In this case, the count number of the X-ray which is measured on the X-ray projection path (measured projection count value) is likely to be a small value. An increase in a thickness projection value error in the case of the small measured projection counter value is as described with reference to FIG. 2. Accordingly, the streak artifacts are considered to be generated due to the large error.

In the embodiment of the present invention, with a concept of the likelihood obtained in consideration of the joint probability density on all of the X-ray projection paths, the thickness of the base substance on the X-ray projection path having a small error is evaluated to be large, and the thickness of the base substance on the X-ray projection path having a large error is evaluated to be small. As a result, it is possible to improve the image quality of the base substance concentration image.

In order to improve the image quality of the base substance concentration image, it is effective to increase an amount of irradiation with the X-ray; however, in a case where the subject is a human body, an X-ray expose dose becomes a problem. Under a condition of the same image quality, the embodiment of the present invention can be expected to more reduce the X-ray expose dose than the comparative example.

6. Procedure of X-Ray CT Image Reconstruction

FIG. 8 is a diagram showing an example of a basic processing procedure for realizing, by a computer, an X-ray CT image reconstruction method according to an embodiment of the present invention. Hereinafter, the basic processing procedure will be described with reference to FIG. 1, in addition to FIG. 8.

A computer to be mentioned below is a computer constituting the X-ray CT image reconstruction device 10 and is connected to the subject capturing device 20 including the X-ray detector that detects the X-ray transmitted through the subject. In addition, the X-ray detector is capable of detecting the X-ray transmitted through a subject, as the detection count value of X-ray, in response to each of N different energy spectra (N is an integer satisfying a relationship of N≥2).

First, the computer acquires, from the subject capturing device 20, the detection count value of the X-ray transmitted through the subject, which is measured by the X-ray detector. The acquired detection count value of the X-ray is associated with a transmission path of the X-ray and an energy spectrum (energy window) and is stored as the measured count projection value 121 in the storage device (storage unit 120) (Step S11).

Next, the computer estimates, for each X-ray transmission path, the thickness of each of M base substances (M is a positive integer satisfying a relationship of M N) constituting the subject, based on the measured count projection value 121 stored in the storage unit 120 (Step S12). A process in Step S12 is a step corresponding to the projection base method of a technology in the related art and corresponds to the processes of the subject•detector model responding unit 101, the first likelihood calculating unit 102, and the likelihood maximization feedback unit 103 in the X-ray CT image reconstruction device 10 according to the embodiment.

In other words, as described with reference to FIG. 1, the computer repeatedly executes the processes of the subject•detector model responding unit 101, the first likelihood calculating unit 102, and the likelihood maximization feedback unit 103. When the likelihood calculated by the first likelihood calculating unit 102 is determined to be the maximum, the thickness of the base substance for each X-ray projection path, which is obtained at the time, is stored as the base substance thickness projection estimation value 124 in the storage device.

Next, the computer estimates, for each X-ray transmission path, the error value regarding the estimated thickness of each of the base substances of the subject based on the detection count value of X-ray (the measured count projection value 121) associated with the X-ray transmission path and the energy spectrum (Step S13). For example, in this estimation, the thickness projection error estimating model curve of the base substance as shown in FIG. 2 is used. In addition, the process in Step S13 corresponds to the process of the base substance error modelling unit 104.

Next, the computer calculates a likelihood which is an index of a probability of a value of an assumed value of the thickness of each of the base substances for each X-ray transmission path with the thickness of each of the base substances for each X-ray transmission path, which has been estimated in Step S12, being set as an initial value (Step S14). In this case, the likelihood is calculated based on the error value regarding the thickness of each of the base substances for each X-ray transmission path, which has been estimated in Step S13. The process in Step S14 corresponds to the process of the second likelihood calculating unit 112.

Although being omitted in the figures, the computer executes the following processes in detail as the process of Step S14.

First, the computer estimates the probability density regarding thicknesses of the base substances for each X-ray transmission path which have been estimated in Step S12, based on the error value regarding the thickness of each of the base substances for each X-ray transmission path, which has been estimated in Step S13. Next, the computer calculates the joint probability density regarding the thicknesses of the base substances for all of X-ray transmission paths, based on the estimated probability density regarding the thicknesses of the base substances for each X-ray transmission path.

Further, the computer calculates the likelihood which is the index of the probability regarding the thickness of each of the base substances for each X-ray transmission path, in accordance with the calculated joint probability density. Consequently, the process of Step S14 is ended. The likelihood can be determined as a value having a one-to-one correspondence with the joint probability density.

Following Step S14, the computer updates the assumed value of the thickness of each of the base substances for each X-ray transmission path such that the likelihood that is estimated in Step S14 increases (Step S15). The process of Step S15 corresponds to the process of the thickness feedback projection calculating unit 113.

The processes of Step S14 and Step S15 described above are repeatedly executed until the likelihood that is calculated in Step S14 is equal to or higher than a predetermined value or until an increase amount of the likelihood is equal to or lower than the predetermined value. In a case where the likelihood is equal to or higher than the predetermined value or the increase amount of the likelihood is equal to or lower than the predetermined value, the back projection is performed on the assumed value of the thickness of each of the base substances for each of the X-ray transmission paths, which has been updated in the Step S15, and the concentration image regarding the base substances contained in the subject is reconstructed (Step S16). The process of Step S16 corresponds to the process of the back projection and concentration feedback unit 114.

As described above, in the process procedure shown in FIG. 8, the joint probability density regarding the thickness of each of the base substances for all of the X-ray transmission paths is considered. Hence, an X-ray CT image obtained by the process procedure shows further improvement in the image quality (for example, refer to FIG. 7), compared to an X-ray CT image that is obtained by the technology in the related art (For example, refer to FIG. 6) without considering the joint probability density.

The present invention is not limited to the embodiments and the modification example described above and includes various modification examples. For example, the embodiments and the modification example are described in detail for easy understanding of the present invention, and the present invention is not limited to absolutely including the entire configurations described above. In addition, it is possible to replace a part of a configuration of an embodiment or modification example with a configuration of another embodiment or modification example, and it is possible to add a configuration of an embodiment or modification example to a configuration of another embodiment or modification example. In addition, it is possible to add, remove, or replace a part of a configuration of each of the embodiments or the modification examples, to, from, or with a configuration included in another configuration or modification example.

REFERENCE SIGNS LIST

10: X-ray CT image reconstruction device
20: subject capturing device
100: thickness error estimating-type projection processor
100a: projection processing unit
101: subject•detector model responding unit (base substance thickness estimating means)
102: first likelihood calculating unit (base substance thickness estimating means)
103: likelihood maximization feedback unit (base substance thickness estimating means)
104: base substance error modelling unit (error estimating means)
110: thickness estimation error using image reconstruction processor
110a: FBP image reconstruction processor
111: forward projection calculating unit
112: second likelihood calculating unit (likelihood calculating means)
113: thickness feedback projection calculating unit (base substance thickness updating means)
114: back projection and concentration feedback unit (base substance concentration image reconstructing means)
120: storage unit (storing means)
121: measured count projection value (detection count value of X-ray)
122: assumed count projection value
123: first base substance thickness projection assumed value
124: base substance thickness projection estimation value
125: base substance thickness projection estimation error value
126: base substance concentration image assumed value
127: second base substance thickness projection assumed value
128: base substance concentration image estimation value
128a: base substance concentration image estimation value
129: base substance concentration image estimation error value
501: thickness feedback direction vector
502: small area element
503: thickness feedback vector
701: soft tissue
702: high X-ray absorber

The invention claimed is:

1. An X-ray CT image reconstruction device that is connected to an X-ray detector that measures a detection count value of X-ray transmitted through a subject, in response to each of N different energy spectra (N is an integer satisfying a relationship of N≥2), the device comprising:

storing means for storing the detection count value of X-ray which is measured by the X-ray detector, in association with each of X-ray transmission paths and each of the energy spectra when the X-ray is transmitted through the subject;

base substance thickness estimating means for estimating, for each of the X-ray transmission paths, a thickness of each of M base substances (M is a positive integer satisfying a relationship of M≤N) constituting the subject, based on the detection count value of X-ray stored in the storing means;

error estimating means for estimating an error value regarding the thickness of each of the base substances, based on the detection count value of X-ray;

likelihood calculating means for calculating a likelihood which is an index of a probability of an assumed value of a thickness of each of the base substances for each of the X-ray transmission paths with the thickness of each of the base substances for each of the X-ray transmission paths, which has been estimated by the base substance thickness estimating means, as an initial value, based on the error value regarding the thickness of each of the base substances for each of the X-ray transmission paths, which has been estimated by the error estimating means;

base substance thickness updating means for updating the assumed value of the thickness of each of the base substances for each of the X-ray transmission paths such that a likelihood that is to be calculated by the likelihood calculating means increases; and base substance concentration image reconstructing means for reconstructing a base substance concentration image regarding the M base substances of the subject by performing back projection of the assumed value of the thickness of each of the base substances for each of the X-ray transmission paths, which has been updated by the base substance thickness updating means.

2. The X-ray CT image reconstruction device according to claim 1, wherein the likelihood calculating means
estimates probability density regarding the thickness of each of the base substances for each of the X-ray transmission paths, based on the error value regarding the thickness of each of the base substances for each of the X-ray transmission paths, which has been estimated by the error estimating means,
calculates joint probability density regarding the thickness of each of the base substances for all of the X-ray transmission paths, based on the estimated probability density regarding the thickness of each of the base substances for each of the X-ray transmission paths, and calculates the likelihood in accordance with the calculated joint probability density.

3. The X-ray CT image reconstruction device according to claim 2,
wherein the base substance thickness updating means updates the thickness of each of the base substances for each of the X-ray transmission paths, based on a likelihood difference between an average value likelihood and an assumed value likelihood, the average value likelihood being a likelihood obtained by applying, to the joint probability density, an average value of thicknesses of the base substances on all of the X-ray transmission paths, which have been estimated by the base substance thickness estimating means, the assumed value likelihood being a likelihood obtained by applying, to the joint probability density, the assumed value of the thickness of each of the base substances, which is different from the average value of the thicknesses of the base substances.

4. An X-ray CT image reconstruction method that causes a computer connected to an X-ray detector that measures a detection count value of X-ray transmitted through a subject, in response to each of N different energy spectra (N is an integer satisfying a relationship of N≥2) to execute:
a first step of storing, in a storage device, the detection count value of X-ray which is measured by the X-ray detector, in association with each of X-ray transmission paths and each of the energy spectra when the X-ray is transmitted through the subject;
a second step of estimating, for each of the X-ray transmission paths, a thickness of each of M base substances (M is a positive integer satisfying a relationship of M≤N) constituting the subject, based on the detection count value of X-ray stored in the storage device;
a third step of estimating an error value regarding the thickness of each of the base substances, based on the detection count value of X-ray;
a fourth step of calculating a likelihood which is an index of a probability of an assumed value of a thickness of each of the base substances for each of the X-ray transmission paths with the thickness of each of the base substances for each of the X-ray transmission paths, which has been estimated in the second step, as an initial value, based on the error value regarding the thickness of each of the base substances for each of the X-ray transmission paths, which has been estimated in the third step;
a fifth step of updating the assumed value of the thickness of each of the base substances for each of the X-ray transmission paths such that a likelihood that is to be calculated in the fourth step increases; and a sixth step of reconstructing a base substance concentration image regarding the M base substances of the subject by performing back projection of the assumed value of the thickness of each of the base substances for each of the X-ray transmission paths, which has been updated in the fifth step.

5. The X-ray CT image reconstruction method according to claim 4,
wherein the computer, in the fourth step,
estimates probability density regarding thicknesses of the base substances for each of the X-ray transmission paths, based on the error value regarding the thickness of each of the base substances for each of the X-ray transmission paths, which has been estimated in the third step;
calculates joint probability density regarding the thicknesses of the base substances for all of the X-ray transmission paths, based on the estimated probability density regarding the thicknesses of the base substances for each of the X-ray transmission paths, and
calculates the likelihood in accordance with the calculated joint probability density.

6. The X-ray CT image reconstruction method according to claim 5,
wherein the computer, in the fifth step,
updates the thickness of each of the base substances for each of the X-ray transmission paths, based on a likelihood difference between an average value likelihood and an assumed value likelihood, the average value likelihood being a likelihood obtained by applying, to the joint probability density, an average value of thicknesses of the base substances on all of the X-ray transmission paths, which have been estimated in the second step, the assumed value likelihood being a likelihood obtained by applying, to the joint probability density, the assumed value of the thickness of each of the base substances, which is different from the average value of the thicknesses of the base substances.

7. An X-ray CT apparatus comprising:
an X-ray tube configured to irradiate a subject with an X-ray;
an X-ray detector configured to measure a detection count value of X-ray with which irradiation from the X-ray tube is performed and which is transmitted through the subject, in response to a plurality of different energy spectra; and
the X-ray CT image reconstruction device according to claim 1.

* * * * *